US006426089B1

(12) United States Patent
Sunohara et al.

(10) Patent No.: US 6,426,089 B1
(45) Date of Patent: Jul. 30, 2002

(54) MULTILAYERED SOFT CAPSULE FOR ELIMINATING BAD BREATH AND PROCESS FOR PRODUCING THE SAME

(75) Inventors: Hideki Sunohara; Ryosei Kamaguchi; Masaru Kagawa; Masashi Nishikawa, all of Osaka; Yuko Miura, Itami, all of (JP)

(73) Assignee: Morishita Jintan Co., Ltd., Osaka (JP)

( * ) Notice: Subject to any disclaimer, the term of this patent is extended or adjusted under 35 U.S.C. 154(b) by 0 days.

(21) Appl. No.: 09/508,304

(22) PCT Filed: Sep. 9, 1998

(86) PCT No.: PCT/JP98/04032

§ 371 (c)(1),
(2), (4) Date: Apr. 28, 2000

(87) PCT Pub. No.: WO99/12516

PCT Pub. Date: Mar. 18, 1999

(30) Foreign Application Priority Data

Sep. 10, 1997 (JP) .............................................. 9-245212

(51) Int. Cl.[7] .............................. A61K 9/48; A61K 9/00
(52) U.S. Cl. ........................ 424/451; 424/400; 424/455; 424/456; 424/457; 424/463
(58) Field of Search ................................. 424/400, 451, 424/455, 456, 457, 463, 489, 490; 514/900, 902, 962, 963

(56) References Cited

U.S. PATENT DOCUMENTS

| 4,695,466 A | 9/1987 | Morishita et al. |
| 5,059,416 A | 10/1991 | Cherukuri et al. |
| 5,702,723 A | * 12/1997 | Griffin .................. 424/463 |

FOREIGN PATENT DOCUMENTS

| EP | 0 326 963 A1 | 8/1989 |
| JP | 59-131355 A | 7/1984 |
| JP | 61-225115 A | 10/1986 |
| JP | 63-239210 A | 10/1988 |
| JP | 1-275522 A | 11/1989 |
| JP | 3-47041 A | 2/1991 |
| JP | 03-220117 A | 9/1991 |
| JP | 09-028356 A | 2/1997 |

OTHER PUBLICATIONS

International Search Report for PCT/JP98/04032 prepared by JPO dated Dec. 3, 1998.

* cited by examiner

*Primary Examiner*—Gollamudi S. Kishore
*Assistant Examiner*—Charesse L. Evans
(74) *Attorney, Agent, or Firm*—Merchant & Gould P.C.

(57) ABSTRACT

The present invention provides a multi-layered soft capsule for effectively eliminating bad breath, and a method for producing the same. The multi-layered soft capsule (10) for eliminating bad breath of the present invention comprises a first soft capsule composed of a first soft capsule layer (1) and a first soft capsule content (3), and a second soft capsule composed of a second soft capsule layer (2) and a second soft capsule content (4), which is contained in the first soft capsule. Both the contents (3) and (4) contain a component having an effect of eliminating bad breath. The multi-layered soft capsule (10) of the present invention is characterized in that the second soft capsule (2) is solved in a stomach.

1 Claim, 3 Drawing Sheets

MULTILAYERED SOFT CAPSULE FOR ELIMINATING BAD BREATH AND PROCESS FOR PRODUCING THE SAME

This application is a 371 of PCT/JP98/04032 filed Sep. 9, 1998.

TECHNICAL FIELD

The present invention relates to a multi-layered soft capsule for eliminating bad breath, having capsule-in-capsule structure (that is called a multiple structure) and effectively eliminating bad breath.

BACKGROUND ART

Hitherto, oral compositions which are (orally) administered to eliminate bad breath in an oral cavity have been studied for a long period of time, as described in for example Japanese Patent Kokai Publication Hei 3(1991)-220117, and some of them are commercially available. Among them, there may be one effectively eliminating not only normal foul halitosis such as mercaptan odor, but also odor generated by a certain food, including garlic odor (particularly, diarylsulfide odor) and alcoholic odor, because it contains some components for eliminating bad breath.

However, the oral compositions conventionally available do not totally eliminate bad breath originated from the ingested food.

The bad breath is generally believed to be caused by a mixture of odor which is generated in an oral cavity from ingested food, with odor which is returned to the oral cavity from a stomach after digesting food, that is usually called as "returned odor". Therefore, even if the former odor in an oral cavity is eliminated, the bad breath remains because of the presence of the returned odor, generated in a stomach.

In order to completely eliminate bad breath, an administration of at least two types of oral compositions, such as one for eliminating the former odor in the oral cavity and another one for eliminating the latter odor originated from the ingested food (that is "the returned odor") is necessary. However, this was inconvenient and also had a disadvantage that, since the latter composition is also dissolved and masticated together with the former composition in the oral cavity, it is thinned by mixing with saliva and other peptic juice before it reaches the stomach, and the content of effective components is too low to eliminate.

One object of the present invention is to overcome the disadvantage and to provide a capsule for eliminating bad breath, particularly effectively acting to both the odor in the oral cavity and the returned odor form the stomach.

Disclosure Of Invention

As shown in FIG. 1, a multi-layered soft capsule (10) for eliminating bad breath of the present invention comprises a first soft capsule composed of a first soft capsule layer (1) and a first soft capsule content (3), and a second soft capsule composed of a second soft capsule layer (2) and a second soft capsule content (4), which is contained in the first soft capsule. Both the contents (3) and (4) contain a component having an effect of eliminating bad breath. The multi-layered soft capsule (10) of the present invention is characterized in that a second soft capsule (2) is soluble in the stomach.

The present invention also provides a multi-layered soft capsule (10) of which the first and/or second soft capsule layer(s) (1) and /or (2) and/or the content(s) (3) and/or (4) comprises a flavoring component.

Additionally, the present invention provides a method for producing a multi-layered soft capsule for eliminating bad breath, comprising simultaneously extruding a composite jet stream into a cooling solution, wherein the composite jet stream consists of a second soft capsule filling solution extruded through a first nozzle, a second soft capsule layer-forming solution though a second nozzle, a first soft capsule filling solution extruded through a third nozzle and a first soft capsule layer-forming solution extruded through a fourth nozzle, with the first, second, third and fourth nozzles being arranged concentrically, a diameter of the nozzles gradually increasing in a numerical order.

Accordingly, the multi-layered soft capsule (10) of the present invention has two effects of eliminating bad breath, including an immediate effect (a) and a long-lasting effect (b) as explained below, by (oral) administration of one capsule.

(a) The component having an effect of eliminating odor in the oral cavity, which is contained in the first soft capsule content, can immediately eliminate the odor after oral administration (the immediate effect of eliminating bad breath). The first soft capsule layer and/or content encapsulated therein may also contain a flavoring component so that a bitter flavor and the like is sweetened when the capsule is dissolved and masticated in the oral cavity, and therefore, the multi-layered soft capsule has excellent palatability.

(b) The component encapsulated in the second soft capsule reaches the stomach without dissolving and masticating in the oral cavity, as well as without mixing with saliva, other peptic juice and the like, and then dissolves in a stomach to show an effect of eliminating "returned odor" (the long-lasting effect of eliminating bad breath).

BEST MODE FOR CARRYING OUT THE INVENTION

The present invention will briefly be explained as follows.

As shown in FIG. 1, a multi-layered soft capsule (10) for eliminating bad breath of the present invention comprises a first soft capsule and a second soft capsule encapsulated in the first soft capsule. The first soft capsule is composed of a first soft capsule layer (1) and a first soft capsule content (3) containing a component having an effect of eliminating bad breath, wherein the first soft capsule content (3) is encapsulated in the first soft capsule layer (1). The second soft capsule is composed of a second soft capsule layer (2) and a first soft capsule content (4) containing a component having an effect of eliminating bad breath, wherein the second soft capsule content (4) is encapsulated in the second soft capsule layer (2).

A base material for forming the first and second soft capsule layers is not specifically limited as long as it forms a soft capsule layers but including gelatin, agar, or a mixture thereof.

In addition to the base material mentioned above, the material for forming the first and second soft capsule layers of a multi-layered soft capsule according to the present invention may also contain a water-soluble polyol such as sotitol, glycerin and the like, sodium alginate or low methoxyl pectin or one obtained by gelling an aqueous solution of sodium alginate or low methoxyl pecting with a polyvalent ion, preferably bi- or more valent ion or the like. The polyvalent ion can be a salt of polyvalent metal such as bi- or more valent metal, particularly when gelling the aqueous solution of sodium alginate, a water-soluble calcium salt, such as calcium chlorate, calcium phosphate and the like is suitably used, or when gelling low methoxyl pectin, a water-soluble salt, such as calcium, magnesium or the like is suitably used.

In the present invention, the material for forming the first and second soft capsule layers may further contain a flavoring component. The flavoring component includes a sweetening, an acidulant and a bitter flavoring. An example of the sweetening may be aspartame, stevia, saccharin sodium, thaumatin. An example of the acidulant may be citric acid, malic acid, tartaric acid, fumaric acid, An example of the bitter flavoring may be caffeine, naringin. At least one selected from the sweetening, the acidulant and the bitter flavoring may be employed in the layer of the first and second soft capsule as the flavoring component.

The material for forming the first and second soft capsule layers of the multi-layered soft capsule according to the present invention may further contain an adjuvant such as a plasticizer, a preservative, a colorant and a perfume, and the like.

A total amount of the adjuvant and the flavoring component formulated in the material for forming the first and second soft capsule layers may be 0.1 to 50 parts by weight, based on 100 parts by weight of the material for forming the first and second soft capsule layers. Preferably, the flavoring component may be in an amount of 0.1 to 30 parts by weight based on 100 parts by weight of the material.

In order to make the second soft capsule insoluble in an oral cavity and soluble in a stomach, the material for forming the first and second soft capsule layers may further contain a substance such as agar or gum arabic, in an amount of 0.01 to 10% by weight based on the total amount of the adjuvant.

In the multi-layered soft capsule of the present invention, the first soft capsule content enclosed in the first soft capsule contains an edible vegetable oil and a component having an effect of eliminating bad breath in the oral cavity. The edible vegetable oil is added to control the flavor and to improve stability of the multi-layered soft capsule, including palm oil, sunflower oil, safflower oil, sesame oil, rapeseed oil, grape-seed oil, and a mixture thereof. An example of the component having an effect of eliminating bad breath in the oral cavity includes lemon oil, peppermint oil, parsley oil, champignon essence, green tea extract, oolong tea extract, mugwort drawing-extract, apple extract, kaki-fruit extract, ginger essence, and the like, and a mixture thereof.

In the first soft capsule content, the edible vegetable oil may be formulated in an amount of 0 to 99 parts by weight based on 100 parts by weight of the content, and the component having an effect of eliminating bad breath in the oral cavity may be formulated in an amount of 1 part by weight to 100 parts by weight based on 100 parts by weight of the content. Particularly, the edible vegetable oil of above 99 parts by weight is not preferable because the second soft capsule has no effect of eliminating bad breath.

The first soft capsule content may also contain the same flavoring component as described in the material for forming the capsule layers. The flavoring component may be formulated in an amount of 0.01 to 50 parts by weight based on 100 parts by weight of the first soft capsule content.

The first soft capsule content may further contain a colorant and a perfume, which are normally used in the art. An amount of the colorant and the perfume formulated in the first soft capsule content may preferably be not more than 80 parts by weight based on 100 parts by weight of the first soft capsule content.

The second soft capsule content may contain the same type of edible vegetable oil and the component having an effect of eliminating bad breath in the oral cavity, as mentioned hereinbefore, and the colorant and the perfume, if necessary, may be formulated therein.

In the second soft capsule content, the edible vegetable oil may be formulated in an amount of 0 to 99 parts by weight based on 100 parts by weight of the second soft capsule content, and the component having an effect of eliminating bad breath in the oral cavity may be formulated in an amount of 1 part to 100 parts by weight based on 100 parts by weight of the second soft capsule content. A total amount of the colorant and the perfume formulated in the second soft capsule content may preferably be not more than 80 parts by weight based on 100 parts by weight of the second soft capsule content.

In the multi-layered soft capsule of the present invention, a total amount of the first and second soft capsule contents may be 10 to 95 percents by weight, preferably 50 to 90 percents by weight, based on the total weight of the multi-layered soft capsule.

An example of a method for producing a multi-layered soft capsule of the present invention includes a method for molding a seamed capsule; and a method for producing a seamless capsule by using some nozzles arranged concentrically. In the former method, the seamed capsule can be produced by preparing a sheet for the second soft capsule layer with gelatin and the like as the base and drying to obtain a dried sheet; encapsulating the second soft capsule content containing the component having an effect of eliminating bad breath with the dried sheet on a rotary filler to form the second soft capsule; and on a rotary filler, simultaneously encapsulating both the second soft capsule and the first soft capsule content containing the component having an effect of eliminating bad breath with a sheet for the first soft capsule layer preliminary prepared and dried.

A more preferable method for producing the multi-layered soft capsule of the present invention is the latter method using a multiple nozzle, most preferably a quadoruplex nozzle arranged concentrically, which is referred to, for example, Japanese Patent Kokai Publication Sho 59(1984)-131355. With reference to FIG. 2, a best mode for carrying out the method for producing the seamless capsule in a form of a quadoruplex structure (that is normally called as a capsule-in-capsule structure) by using the quadoruplex nozzle arranged concentrically will be illustrated as follows.

A first and second soft capsule filling solutions for the first and second soft capsule contents, and a first and second soft capsule layer-forming solutions for the first and second soft capsule layers are prepared, respectively. As shown in FIG. 2, the second soft capsule filling solution (11') is supplied into a first nozzle (11) from a direction C, the second soft capsule layer-forming solution (12') is supplied into a second nozzle (12) from a direction D, the first soft capsule filling solution (13') is supplied into a third nozzle (13) from a direction A, and then the first soft capsule layer-forming solution (14') is supplied into a outermost fourth nozzle (14) from a direction B. The multi-layered soft capsule (20) of the present invention can be produced by simultaneously extruding the solutions through annular ends of the nozzles, respectively, to make a four-phase composite jet stream, followed by releasing the jet stream into a cooling solution (15).

In the method for producing the capsule of the present invention, since all of the loading materials are liquid, the encapsulation process can be easily performed by adequately vibrating the composite jet stream with a vibration mean to readily release the jet stream, and thereby a particle size of the resulting capsules may be controlled uniformly.

In the multi-layered soft capsule of the present invention, the first soft capsule may be formed into a particle size in a diameter of 2.0 to 20 mm, preferably 3.0 to 10 mm, and a covering population, that is a population of a weight of the first soft capsule layer based on a total weight of the first soft capsule, of 5 to 50% preferably 8 to 30%. The second soft capsule may be formed into a particle size in diameter of 0.5 to 18 mm, preferably 1.0 to 9 mm, and a covering population of 5 to 100%, preferably 8 to 50%.

In the present invention, a multi-layered soft capsule as a final product may be obtained by drying the resulting capsule produced by the above method.

The following Examples further illustrate the present invention in detail but are not to be construed to limit the scope thereto.

EXAMPLES

Example

A first soft capsule layer-forming solution, a first soft capsule filling solution, a second soft capsule layer-forming solution and a second soft capsule filling solution were prepared by mixing materials in each formulation as shown in Table 1. Then, the resulting solutions were charged into an apparatus for forming a seamless capsule manufactured by MORISITA JINTAN CO., LTD., and simultaneously extruded through a quadoruplex nozzle, that is four nozzles were concentrically arranged in the apparatus, respectively, to make a four-phase jet stream, followed by releasing the jet stream into a cooling solution to obtain a multi-layered soft capsule of the present invention in a form of a quadoruplex structure.

TABLE 1

| Formulation | % by weight |
| --- | --- |
| A first soft capsule layer-forming solution: | |
| Gelatin | 9.0 |
| Sweetening: aspartame | 0.2 |
| Sorbitol | 2.0 |
| A first soft capsule filling solution: | |
| Lemon oil | 6.0 |
| Peppermint | 1.0 |
| Perfume: L-menthol, winter-green oil and vanilla oil | 7.0 |
| Sweetening: aspartame | 0.2 |
| Edible vegetable oil: palm oil | 57.3 |
| A second soft capsule layer-forming solution: | |
| Gelatin | 5.0 |
| Sweetening: aspartame | 0.1 |
| A second soft capsule filling solution: | |
| Parsley oil | 6.0 |
| Edible vegetable oil: palm oil | 6.0 |

Comparative Example

A commercial available capsule having no capsule-in-capsule structure (i.e. it is not in a form of a quadoruplex structure), but containing parsley oil therein as a component having an effect of eliminating bad breath, was obtained (from Breath Asure, Inc., in U.S.A., a trade name of "BREATH ASURE").

Evaluation of Effect of Eliminating Bad Breath

For the multi-layered soft capsule from Example and the capsule from Comparative Example, an effect of eliminating bad breath was tested according to the following procedures.

1. Seven subjects and three judges were selected, respectively. The subjects cleaned their teeth without a dentifrice.

2. Each initial breath of the subjects was collected (Breath A).

3. All of the subjects ate pot stickers containing garlic.

4. Each breath of the subjects was collected again (Breath B).

5. The capsules having an effect of eliminating bad breath obtained in Example and Comparative Example were orally administered to the subject separately, not concurrently.

6. Each final breath of the subjects was collected at 0 minute, 30 minutes, 60 minutes and 180 minutes after administration, and then the judges evaluated the final breath compared with Breath A and B according to the following criteria.

Criteria:
 0: Smell-less.
 1: Felt as foul as Breath A.
 2: Felt fouler than Breath A.
 3: Felt not as foul as Breath B.
 4: Felt as foul as Breath B.

After finishing the procedures 1 to 5, the (seven) subjects performed the same procedures again, with the exception of no administration of the capsules for eliminating bad breath. Then, the judges evaluated the breath collected from the subjects for an effect of eliminating bad breath according to the same criteria as described above.

The results are shown in a graph of FIG. 3. In FIG. 3, a period of time after administration of the capsule for eliminating bad breath is shown in axis of abscissas, and an average of the evaluation results by the judges is shown in axis of ordinates, respectively. In FIG. 3, line-a shows results after administration of the multi-layered soft capsule of Example according to the present invention; line-b shows results obtained after administration of the capsule of Comparative Example; and line-c shows results without administration of the capsule.

The results in FIG. 3 show that an average of the evaluation for an effect of emitting bad breath decreases to a value of 2 at 60 minutes after administration of the capsule of Comparative Example (line-b) or no capsules line-c). However, for no administration (line-c), the final breath was felt fouler again by returned odor from the stomach, For the capsule of Comparative Example, when the period after administration is above 60 minutes, the final breath including returned odor was not free of bad breath to a level of the initial breath just after cleaning the teeth.

In contrast, it is also found in FIG. 3 that the multi-layered soft capsule of the present invention shows an immediate effect of eliminating bad breath just after administration, and the effect also continues at 180 minutes after administration.

Figure 1:
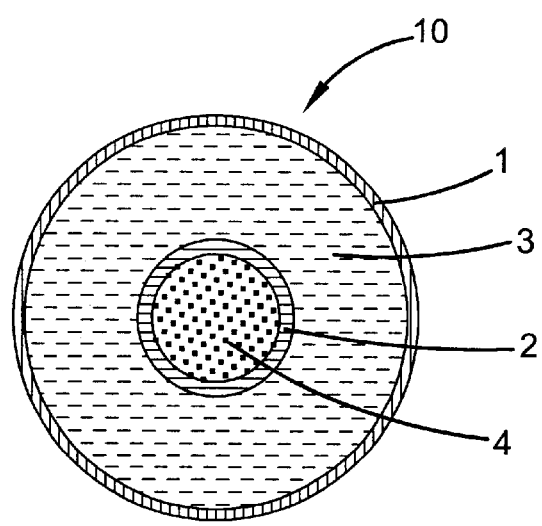
FIG. 1 schematically illustrates a vertical cross sectional view of a multi-layered soft capsule for eliminating bad breath according to the present invention.
Figure 2:
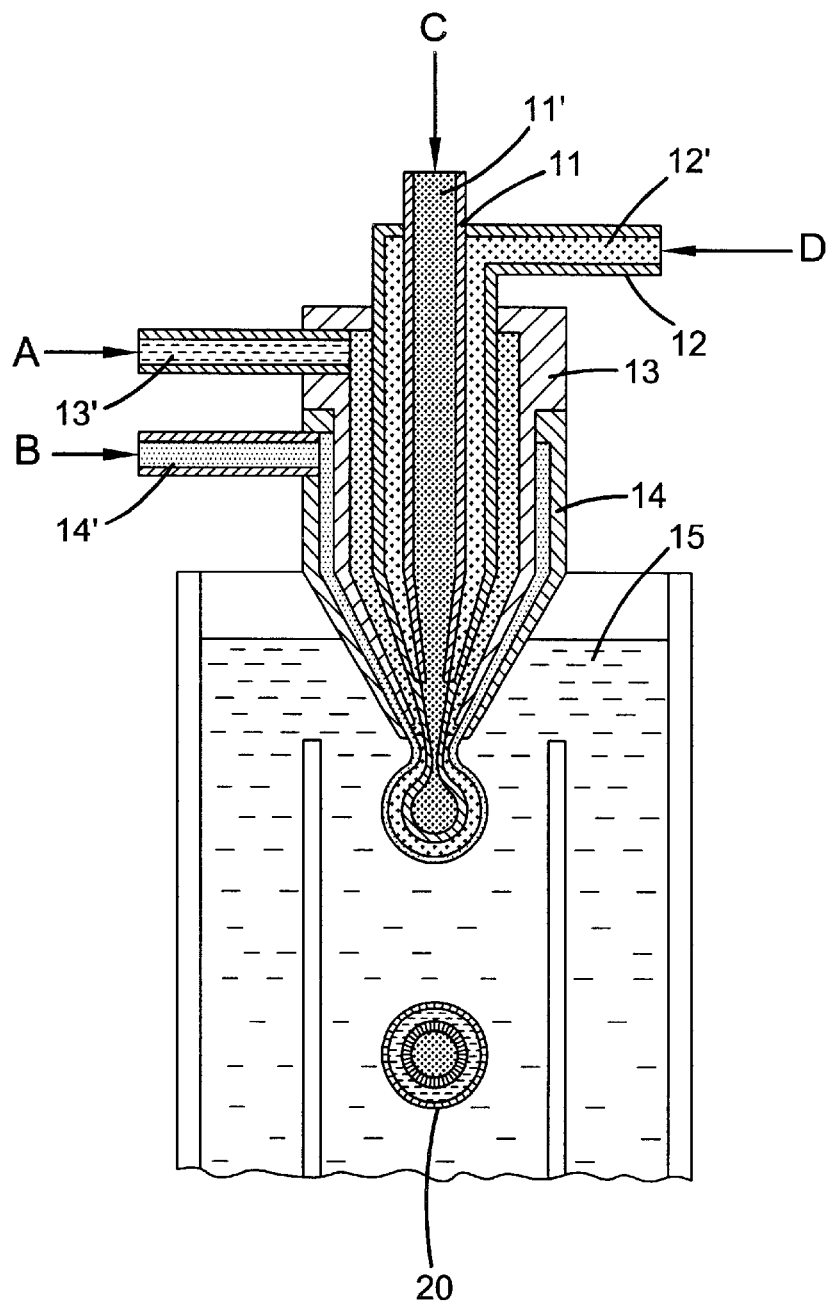
FIG. 2 schematically illustrates a vertical cross sectional view of one embodiment of nozzles in a suitable apparatus for producing the multi-layered soft capsule for eliminating bad breath according to the present invention.
Figure 3:
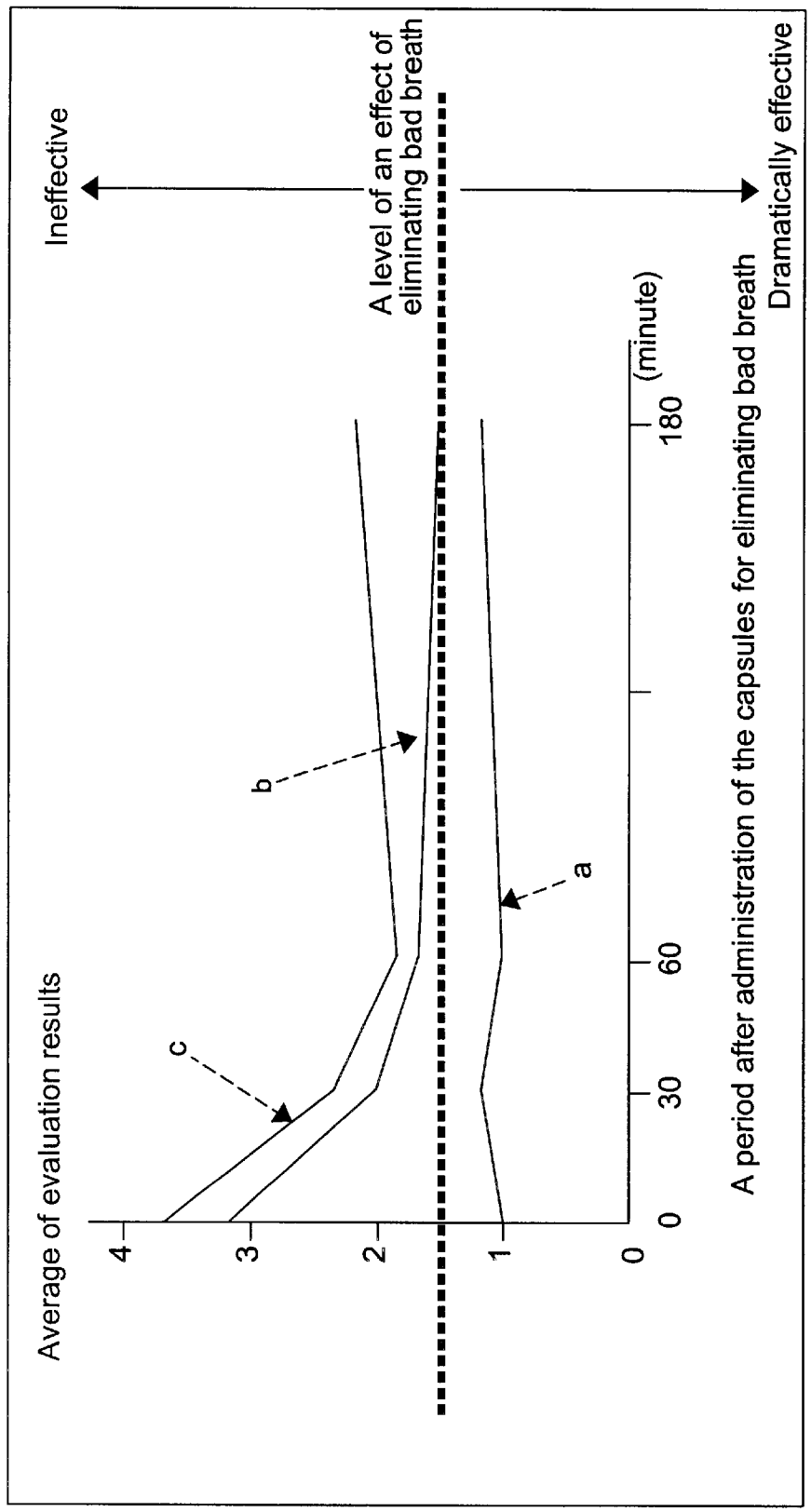
FIG. 3 is a graph illustrating results for an effect of eliminating bad breath on subjects.

What is claimed is:

1. A method for producing a multi-layered soft capsule for eliminating bad breath, comprising simultaneously extruding a second soft capsule filling solution through a first nozzle, a second soft capsule layer-forming solution through a second nozzle, a first soft capsule filling solution through a third nozzle and a first soft capsule layer-forming solution through a fourth nozzle to make a composite jet stream, followed by releasing the jet stream into a cooling solution, wherein the first, second, third and fourth nozzles are arranged concentrically, a diameter of the nozzles gradually increasing in a numerical order.

* * * * *